United States Patent
Front

(10) Patent No.: US 6,173,201 B1
(45) Date of Patent: Jan. 9, 2001

(54) STEREOTACTIC DIAGNOSIS AND TREATMENT WITH REFERENCE TO A COMBINED IMAGE

(75) Inventor: Yaron Front, Haifa (IL)

(73) Assignee: V-Target Ltd., Haifa (IL)

(*) Notice: Under 35 U.S.C. 154(b), the term of this patent shall be extended for 0 days.

(21) Appl. No.: 09/253,779

(22) Filed: Feb. 22, 1999

(51) Int. Cl.[7] .................................................. A61B 5/00
(52) U.S. Cl. ........................................... 600/429; 606/130
(58) Field of Search ................................... 600/407, 411, 600/414, 417, 426, 427, 429, 431, 436; 606/130

(56) References Cited

U.S. PATENT DOCUMENTS 5,376,795   12/1994   Hasegawa et al. .

OTHER PUBLICATIONS

Blankespoor et al, "Attenuation Correction of SPECT Using X–Ray CT on an Emission–Transaction CT System: Myocardial Perfusion Assessement", *Trans. Nucl, Sci.*, 43(4): 2263–2274.

Kalki et al, "Myocardial Perfusion Imaging with a Combined X–Ray CT and SPECT System", *J. Nucl. Med.*, 38(10): 1535–1540, 1997.

Blankespoor et al, "Development of an Emission–Transaction CT System Combining X–Ray CT and SPECT", *IEEE Trans. Nucl. Sci.*, pp 1758–1761, 1995.

Lang et al, "Description of a Prototype Emission–Transmissions Computed Tomography maging System", *J. Nucl. Med.*, 33:1881–1887, 1992.

Mueller et al, Interventional Radiology in the Chest and Abdomen, *New England J. Med.*, 322(19): 1364–1374, 1990.

Pagani, J.J., "Biopsy of Focal Hepatic Lesions", *Radiology*, 147: 673–675, 1983.

Yankaskas et al, "Delayed Complications from Fine–Needle Biopsies of Solid Masses of the Abdomen", *Invest.Radiol.*, 21:325–328, 1986.

Mueller et al, "Severe Acute Pancreatitis After Percutaneous Biopsy of the Pancreas", *AJR*, 151: 493–494, 1988.

Nickers et al, "Modern Brachytherapy: Current State and Future Prospects", *Europ. J. Cancer*, 33(11): 1747–1751, 1997.

Bodner et al, "Brachytherapy and Pancreatic Cancer", *Sem in Surg. Oncol.*, 13:204–207, 1997.

Hilaris et al, "Role of Brachytherapy in Adult Soft Tissue Sarcomas", *Sem in Surg. Oncol.*, 13: 196–203, 1997.

Raben et al, "Brachytherapy for Non–Small Cell Lung Cancer and Selected Neoplasms of the Chest", *Chest*, 112: 276S–286S, 1997.

Tian et al, "Ultrasound–Guided Internal Radiotherapy Using Yttrium–90–Glass Microspheres for Liver Malignancies", *J. Nucl. Med*, 37: 958–963, 1996.

Zeller et al, "Interstitial Chemotherapy of Experimental Gliomas", *Cancer Treatment Research*, 17:181–189.

*Primary Examiner*—William E. Kamm

(57) ABSTRACT

A method of stereotactic therapy. A frame including at least three markers that are imaged by a structural imaging modality such as CT or MRI, is rigidly secured to a patient and a structural image, of a target inside the patient including diseased tissue, and of a part of the frame including the markers, is acquired. A functional image, such as a SPECT image or a PET image, of the diseased tissue is acquired and registered with the structural image to produce a combined image. A stereotactic guide is rigidly attached to the frame and is used to guide an instrument such as a biopsy needle or a brachytherapy needle to the diseased tissue, with reference to the combined image.

10 Claims, 3 Drawing Sheets

STEREOTACTIC DIAGNOSIS AND TREATMENT WITH REFERENCE TO A COMBINED IMAGE

FIELD AND BACKGROUND OF THE INVENTION

The present invention relates to the diagnosis and treatment of ailments such as cancer and, more particularly, to a method of stereotactic diagnosis and treatment with reference to an image of the target region of the patient that combines a high-resolution structural image such as a CT or MRI image with a lower resolution functional image such as a nuclear image.

Several diagnostic and therapeutic techniques that are used to diagnose or treat cancer involve the insertion of an instrument such as a needle, from outside the patient, into a tumor that is suspected of being cancerous. For example, a biopsy needle commonly is inserted into the tumor to withdraw a tissue sample for biopsy. In brachytherapy, a radioisotope is placed at the tip of a needle, and the tip of the needle is inserted into the tumor to deliver radiation to the tumor with minimal irradiation of the surrounding healthy tissue. Chemotherapeutic agents also may be injected into the tumor using a needle. The needles often are inserted into the patient with reference to a series of structural images of the patient, such as ultrasound images or CT images. These images are acquired before and during the insertion of the instrument, to verify that the instrument is being directed towards the correct target and is bypassing organs such as blood vessels which should not be penetrated by the instrument.

A tumor may include both cancerous tissue and non-cancerous tissue. It would be useful to be able to direct an instrument specifically to a cancerous portion of a tumor, and to avoid an obviously non-cancerous portion of a tumor. In the case of a biopsy, the needle should be directed towards the portion of the tumor that is most likely to be cancerous. In the case of brachytherapy, the needle should be directed towards the portion of the tumor that is known to be cancerous. Structural imaging modalities, such as CT and MRI, that have enough spatial accuracy and resolution to distinguish resolve tumors, are nevertheless unable to differentiate cancerous tissue from noncancerous tissue because they resolve only structure. Functional imaging modalities, including tomographic nuclear imaging modalities such as SPECT and PET, can distinguish cancerous tissue from noncancerous tissue but lack the spatial accuracy and resolution that is needed for the accurate positioning of instruments such as biopsy needles and brachytherapy needles.

It is known to register a functional image with a structural image to produce a combined image. See, for example, M. W. Vannier and D. E. Gayou, "Automated registration of multimodality images", *Radiology*, vol. 169 pp. 860–861 (1988); J. A. Correia, "Registration of nuclear medicine images, *J. Nucl. Med.*, vol. 31 pp. 1227–1229 (1990); J-C Liehn, A. Loboguerrero, C. Perault and L. Demange, "superposition of computed tomography and single photon emission tomography immunoscinigraphic images in the pelvis: validation in patients with colorectal or ovarian carcinoma recurrence", *Eur. J. Nucl. Med.*, vol. 19 pp. 186–194 (1992); F. Thomas et al., "Description of a prototype emission transmission computed tomography imaging system", *J. Nucl. Med.*, vol. 33 pp. 1881–1887 (1992); D. A. Weber and M. Ivanovic, "Correlative image registration", *Sem. Nucl. Med.*, vol. 24 pp. 311–323 (1994); and Hasegawa et al., U.S. Pat. No. 5,376,795. All six of these prior art documents are incorporated herein by reference for all purposes as if fully set forth herein. In principle, a sequence of such combined images could be used to direct an instrument to the cancerous portion of a tumor. In practice, the multiple imaging sessions and registrations that this would require make this solution impractical and possibly dangerous.

Stereotaxis is a known technique for localizing a region inside the body of a patient from outside the body of the patient, and for directing an instrument such as a needle, or a narrow beam of therapeutic radiation, to the target region. The degree of accuracy needed for stereotaxis is relatively high, so that the technique has been considered useful mainly on the brain and the breast. For example, in stereotactic radiosurgery of the brain, a CT localization frame is attached rigidly to the head of a patient and a CT image of the patient's brain is acquired with the CT localization frame in place. The position of the CT localization frame in the CT image is used to position the patient with respect to the source of the beam of radiation so that the beam intersects the desired target. Note that the CT localization frame is removed from the patient's head before the therapeutic irradiation commences.

There is thus a widely recognized need for, and it would be highly advantageous to have, a method of stereotactic diagnosis and therapy that could be used to direct a diagnostic or therapeutic instrument to a cancerous portion of a tumor located in a portion of a patient other than the patient's head or breast.

DEFINITIONS

As used herein, the term "target" refers to a structurally discrete portion of the patient, such as an organ or a tumor, that is suspected of including diseased tissue but that also may include healthy or noncancerous tissue.

As used herein, the term "therapeutic instrument" refers to an instrument that is inserted in the target from outside the patient for the purpose of either diagnosis of disease or treatment of disease. Typical examples of therapeutic instruments include biopsy needles and needles for brachytherapy and chemotherapy.

SUMMARY OF THE INVENTION

According to the present invention there is provided a method for diagnosing and accessing a target in a patient, including the steps of: (a) rigidly securing a frame to the patient, the frame including at least three markers; (b) imaging at least a portion of the patient including the target, using a structural imaging modality, to produce a structural image of the at least portion of the patient and of the markers; (c) imaging the at least portion of the patient using a functional imaging modality to produce a functional image of the at least portion of the patient; and (d) if a presence of a diseased portion of the target is indicated in the functional image: (i) registering the functional image with the structural image to produce a first combined image, (ii) rigidly attaching a stereotactic guide to the frame, and (iii) directing a therapeutic instrument to the diseased portion of the target, using the stereotactic guide, with reference to the diseased portion and to the markers as imaged on the first combined image.

Although the scope of the present invention includes the diagnosis and treatment of any diseased tissue, the present invention is described below in terms of the primary application thereof, the diagnosis and treatment of cancer.

In the first phase of the present invention, a frame is rigidly attached to the patient and a portion of the patient including the target is imaged using a high-resolution structural imaging modality such as CT or MRI. The frame includes markers that are recorded in the structural image so that the position of any other point in the image relative to the frame can be determined.

In the second phase of the present invention, a suitable radiopharmaceutical, that is taken up preferentially by cancerous tissue, is injected into the patient, and the portion of the patient that was imaged in the first phase is again imaged using a lower-resolution, functional imaging modality that records the radiation emitted by the radiopharmaceutical to give an image of the cancerous part of the target. The structural image and the functional image are registered to provide a combined image that shows which part of the tumor mass contains cancer and where the cancerous areas are on the high-resolution image.

In the third phase of the present invention, a stereotactic guide is rigidly attached to the frame. Because the position of the cancerous tissue relative to the frame is known, the position of the cancerous tissue relative to the stereotactic guide also is known. The stereotactic guide then is used, under computer control, to guide an instrument such as a biopsy needle or a brachytherapy needle to the cancerous tissue, with reference to the pixels of the combined image that represent the markers and the cancerous tissue. The trajectory of the instrument is programmed in advance so that the instrument does not penetrate organs, such as vascular structures, that should not be penetrated.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method of stereotactic diagnosis and treatment of diseased tissue. Specifically, the present invention can be used to diagnose and treat cancerous tissue in tumors.

The principles and operation of stereotactic therapy according to the present invention may be better understood with reference to the drawings and the accompanying description.

Figure 1:
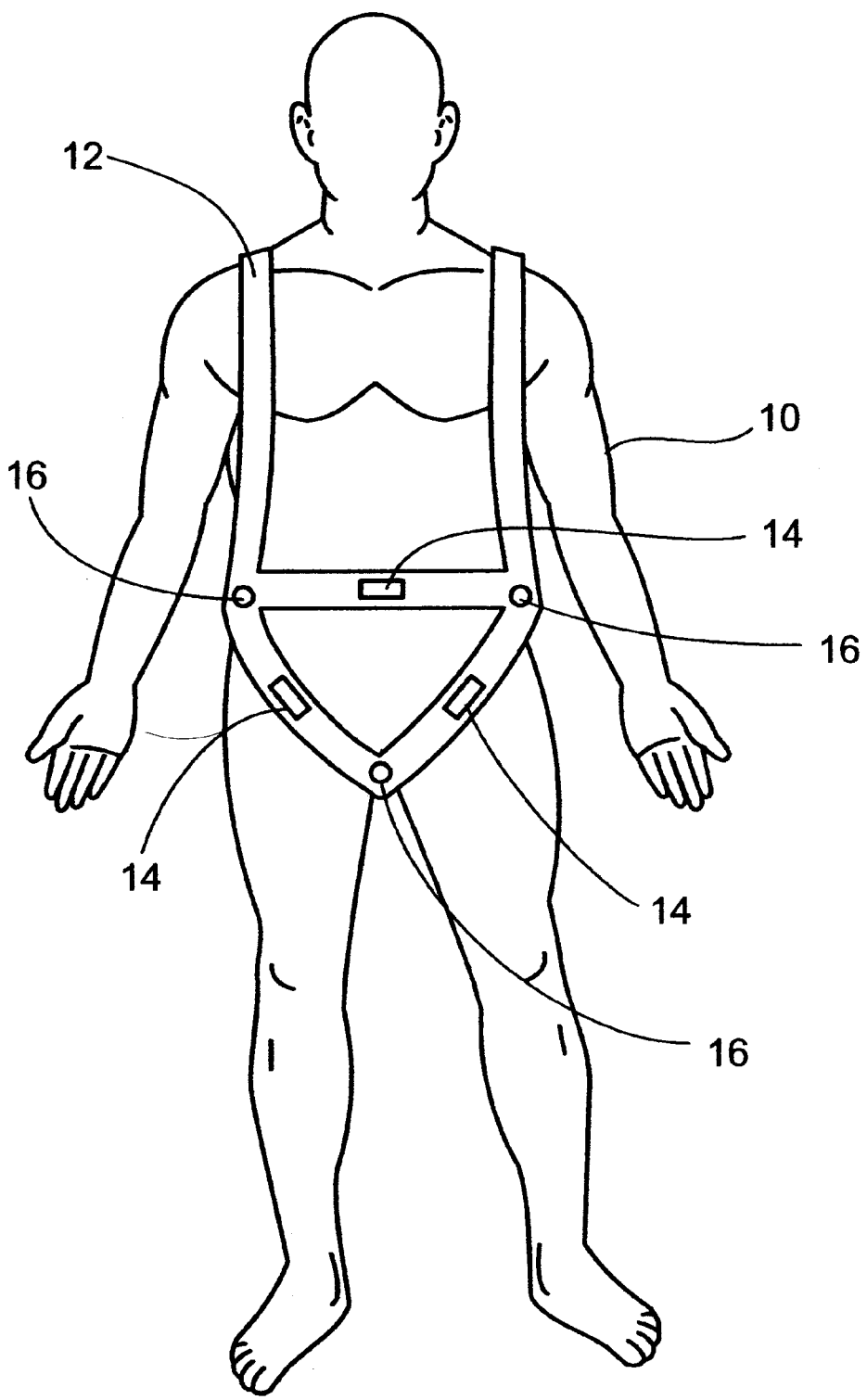
FIG. 1 shows a patient wearing a frame.

Referring now to the drawings, FIG. 1 shows a patient 10 wearing a rigid frame 12. By virtue of being snugly fitted to the shoulders, waist and groin of patient 10, frame 12 is rigidly secured to patient 10. Frame 12 bears thereon three markers 14 that include a material that shows up well in a high-resolution structural image of patient 10 and frame 12. For example, if CT is used for structural imaging, markers 14 are lead blocks. If MRI is used for structural imaging, markers 14 are hollow plastic blocks filled with a solution of Gd-DTPA. Frame 12 also bears three attachment points 16 for a stereotactic guide. A high-resolution structural image of the portion of patient 10 that contains the target is acquired while patient 10 wears frame 12 as shown in FIG. 1.

Three is the minimum number of markers 14 that is needed for accurate recording of the relative positions of frame 12 and the internal tissues of patient 10 in three dimensions in the structural image. Markers 14 are shown in FIG. 1 as three blocks only for illustrational clarity. Any suitable marker geometry or form may be used, for example, vertical and diagonal rods, as are used in the BRW CT localization frame sold by Radionics. Inc., of Burlington Mass. and by Sofamor Danek, of Elektra, Sweden, for stereotactic treatment of the brain. The positioning of markers 14 and attachment points 16 on frame 12 in FIG. 1 also is only illustrative, as an example of appropriate positions of markers 14 and attachment points 16 for treatment of the abdomen of patient 10.

Subsequent to, or simultaneously with, the acquisition of a high-resolution structural (e.g., CT or MRI) image of the portion of patient 10 that includes the target, a lower resolution functional (e.g., nuclear medicine) image of the same portion of patient 10 is acquired for the purpose of imaging the diseased tissue in the target. If the disease under treatment is cancer, then the preferred imaging modality is nuclear imaging, and the patient is injected before imaging with a radiopharmaceutical that is preferentially taken up by cancerous tissue. Examples of such radiopharmaceuticals include Ga-67, Tc-99m MIBI, Tl-201, F-18 fluorodeoxyglucose and In-111 octreotide. The most preferred nuclear imaging modalities are tomographic modalities such as SPECT and PET. The functional and structural images then are registered, for example as described in the paper by Weber and Ivanovic cited above, to produce a combined image.

Figures 2A, 2B, 2C:
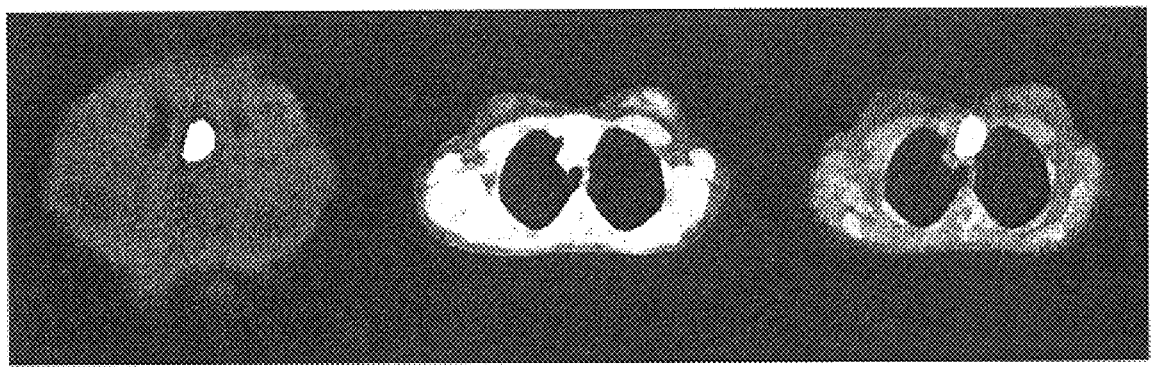
FIGS. 2A, 2B and 2C are axial sections of a Ga-67, a CT and a combined image of a chest of a patient.

FIG. 2A is an axial section of a Ga-67 image of a chest of a cancer patient, showing a tumor (yellow) containing a lymphoma (red). FIG. 2B is an axial section of a CT image of the same patient's chest. The portion of FIG. 2B that corresponds to the lymphoma of FIG. 2A is outlined in yellow in FIG. 2B. It can be seen that there is no visual contrast in FIG. 2B between the lymphoma and the rest of the tumor. FIG. 2C is an axial section of a combined image, showing the functional image of FIG. 2A registered on the structural image of FIG. 2B. FIG. 2C was produced by registering the image of FIG. 2A with the image of FIG. 2B as described in the paper by Weber and Ivanovic cited above. Biopsy and therapy directed towards the tumor should be aimed specifically at the lymphoma.

Figure 3:
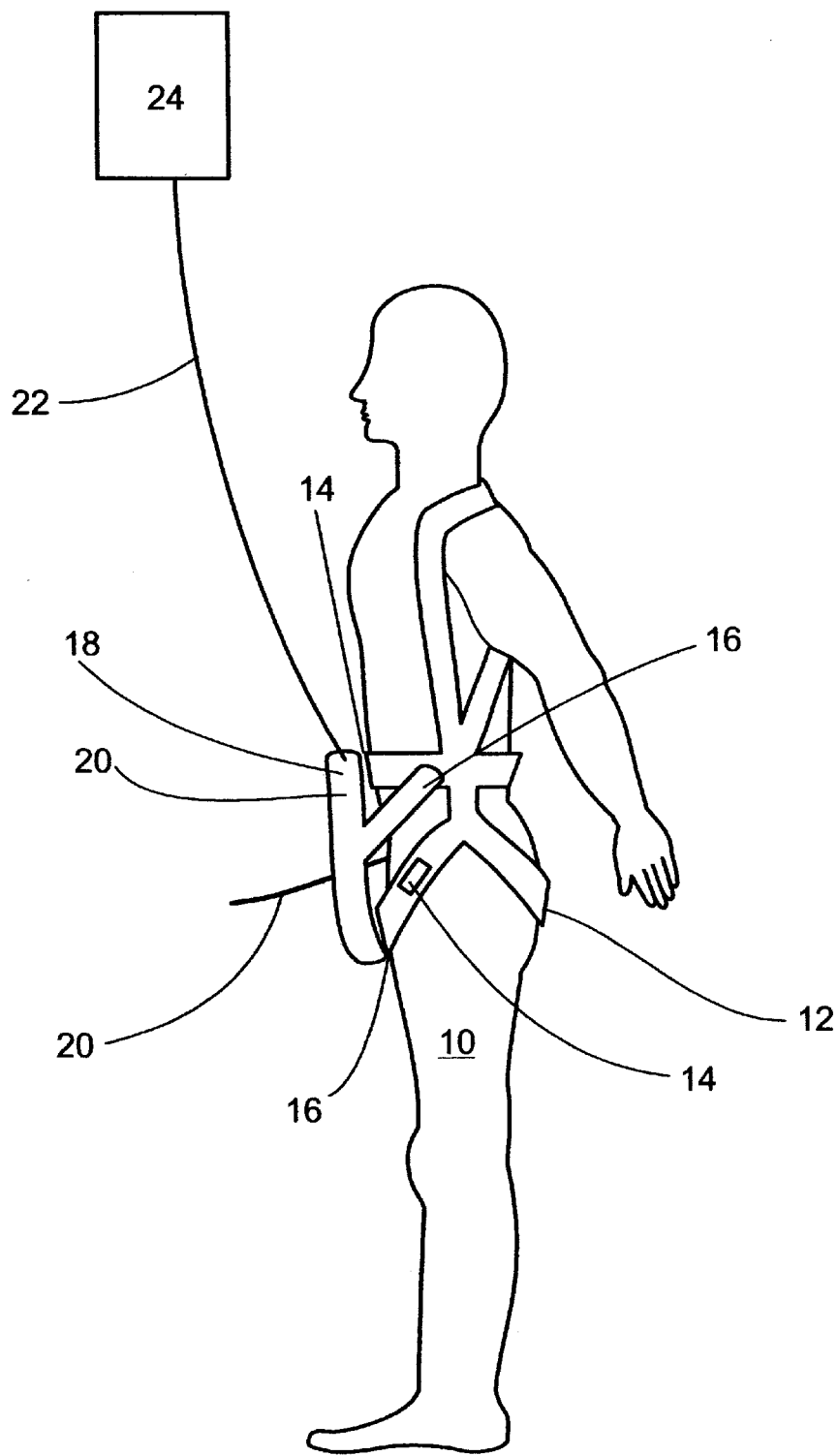
FIG. 3 shows the patient of FIG. 1 with a stereotactic guide attached to the frame.

FIG. 3 shows patient 10 with a stereotactic guide 18 firmly and rigidly attached to frame 12 at attachment points 16, and with an instrument 20, such as a biopsy needle or a brachytherapy needle, mounted in stereotactic guide 18 and ready for insertion into the abdomen of patient 10 under the control of a computer 24. Computer 24 sends control signals, including the relevant Cartesian coordinates, to stereotactic guide 18 via a suitable electrical connection such as a cable 22. Computer 24 also includes a suitable display mechanism, such as a video terminal, for displaying the combined image. A physician programs the trajectory of instrument 22 in computer 24 in advance, with reference to the position of the target and the other internal organs of patient 10, with reference to the diseased tissue in the target, and with reference to markers 14, as seen in the combined image. Computer 24 includes software that transforms the coordinate system of the combined image, as defined by markers 14, into the coordinate system of stereotactic guide 18. This software is used to transform the coordinates of the trajectory, which is defined by the physician in the coordinate system of the combined image, into the coordinate system of stereotactic guide 18, to enable stereotactic guide 18 to steer instrument 20 along the desired trajectory. The physician designs the trajectory to avoid vascular structures and other organs that should not be penetrated by instrument 20.

To assist the physician in recognizing and avoiding vascular structures such as blood vessels, another functional image of the portion of patient 10 that includes the target is acquired, for the purpose of imaging the blood vessels. The preferred imaging modality for imaging vascular structures is Tc-99m labeled red blood cells SPECT. For this purpose, patient 10 is first injected with Tc-99m, to label the red blood cells of patient 10. The SPECT image of the vascular structures is registered with the structural image, and the resulting second combined image is displayed by computer 24 and is used by the physician in planning the trajectory of instrument 20 to avoid penetration of the imaged vascular structures.

Similarly, to assist the physician in recognizing and avoiding organs such as the kidneys, another functional image of the portion of patient 10 that includes the target is acquired. In the specific case of the kidneys, this second functional image is a SPECT image obtained using Tc-99 DMSA. The SPECT image of the organ or organs is registered with the structural image, and the resulting second combined image is displayed by computer 24 and is used by the physician in planning the trajectory of instrument 20 to avoid penetration of the imaged organs. To prevent errors in planning the trajectory of instrument 20, computer 24 is programmed to avoid penetration of blood vessels and organs with high blood pool, and other organs that should not be penetrated, such as the gut, the kidneys, the pancreas and the heart.

While the invention has been described with respect to a limited number of embodiments, it will be appreciated that many variations, modifications and other applications of the invention may be made.

What is claimed is:

1. A method for diagnosing and accessing a target in a patient, comprising the steps of:
   (a) rigidly securing a frame to the patient, said frame including at least three markers;
   (b) imaging at least a portion of the patient including the target, using a structural imaging modality, to produce a structural image of said at least portion of the patient and of said markers;
   (c) imaging said at least portion of the patient using a functional imaging modality to produce a functional image of said at least portion of the patient; and
   (d) if a presence of a diseased portion of the target is indicated in said functional image:
       (i) registering said functional image with said structural image to produce a first combined image,
       (ii) rigidly attaching a stereotactic guide to said frame, and
       (iii) directing a therapeutic instrument to said diseased portion of the target, using said stereotactic guide, with reference to said diseased portion and to said markers as imaged on said first combined image.

2. The method of claim 1, wherein said structural imaging modality is selected from the group consisting of CT and MRI.

3. The method of claim 1, wherein said functional imaging modality is a nuclear imaging modality.

4. The method of claim 3, wherein said nuclear imaging modality is selected from the group consisting of SPECT and PET.

5. The method of claim 3, wherein said nuclear imaging modality images radiation emitted by a radiopharmaceutical inside the target.

6. The method of claim 5, wherein said radiopharmaceutical is selected from the group consisting of Ga-67, Tc-99m MIBI Tl-201, F-18 fluorodeoxyglucose and In-111 octreotide.

7. The method of claim 1, further comprising the steps of:
   (e) imaging at least one vascular structure in said at least portion of the patient to produce a vascular structure image; and
   (f) registering said vascular structure image with said structural image to produce a second combined image;
and wherein said directing of said therapeutic instrument to said diseased portion of the target is effected with reference to said at least on one vascular structure as imaged in said second combined image.

8. The method of claim 7, wherein said imaging of said at least one vascular structure is effected by SPECT imaging of red blood cells labeled by Tc-99m.

9. The method of claim 1, further comprising the step of:
   (e) imaging at least one organ in said at least portion of the patient to produce an organ image; and
   (f) registering said organ image with said structural image to produce a second combined image;
and wherein said directing of said therapeutic instrument to said diseased portion of the target is effected with reference to said at least one organ as imaged in said second combined image.

10. The method of claim 9, wherein said imaging of said at least one organ includes SPECT imaging using Tc-99m DMSA.

* * * * *